United States Patent [19]

Bonutti

[11] Patent Number: 5,503,619
[45] Date of Patent: *Apr. 2, 1996

[54] ORTHOSIS FOR BENDING WRISTS

[76] Inventor: Peter M. Bonutti, 1303 W. Evergreen Plz., Effingham, Ill. 62301

[ * ] Notice: The portion of the term of this patent shall not extend beyond the expiration date of Pat. No. 5,395,303.

[21] Appl. No.: 306,619

[22] Filed: Sep. 15, 1994

Related U.S. Application Data

[60] Continuation-in-part of Ser. No. 126,081, Sep. 23, 1993, Pat. No. 5,395,303, which is a division of Ser. No. 690,845, Apr. 24, 1991, Pat. No. 5,285,773, which is a continuation-in-part of Ser. No. 559,700, Jul. 30, 1990, Pat. No. 5,167,612, and a continuation-in-part of Ser. No. 686,811, Apr. 17, 1991, Pat. No. 5,213,094.

[51] Int. Cl.$^6$ ..................................................... A61F 5/00
[52] U.S. Cl. .................... 602/16; 602/20; 601/33
[58] Field of Search ............................ 602/5, 16, 20–22; 128/898; 601/23, 33, 40

[56] References Cited

U.S. PATENT DOCUMENTS

| | | |
|---|---|---|
| 2,832,334 | 4/1958 | Whitelaw .................................. 601/33 |
| 4,285,773 | 2/1984 | Bonutti et al. . |
| 4,538,595 | 9/1985 | Hajianpour . |
| 5,327,882 | 7/1994 | Saringer et al. ........................... 601/40 |
| 5,364,323 | 11/1994 | Liu ....................................... 601/40 X |
| 5,395,303 | 3/1995 | Bonutti et al. ....................... 602/23 X |

Primary Examiner—Linda C. M. Dvorak
Attorney, Agent, or Firm—Tarolli, Sundheim & Covell

[57] ABSTRACT

The same orthosis can be sequentially used to bend different wrists. The orthosis may be used to bend a first wrist in flexion and a second wrist in extension. When the orthosis is to be used to bend a wrist in flexion, a pair of cuffs and cuff arms are connected with a forearm and hand with the orthosis in a first orientation relative to the wrist. At this time, the cuff arms and an actuator mechanism are disposed in an inner sector disposed adjacent to a palm side of the hand. When the orthosis is to be used to bend the wrist in extension, the orthosis is mounted on the forearm and hand in a second orientation with the cuff arms and actuator mechanism in an outer sector adjacent to the back side of the hand. During operation of the orthosis, force is transmitted from an input member through an actuator mechanism to the cuff arms to pivot the cuff arms about spaced apart parallel axes. At the same time, force is transmitted from the actuator mechanism to the cuffs to move the cuffs along the cuff arms in a direction toward the wrist and axes about which the cuff arms are pivoted.

50 Claims, 8 Drawing Sheets

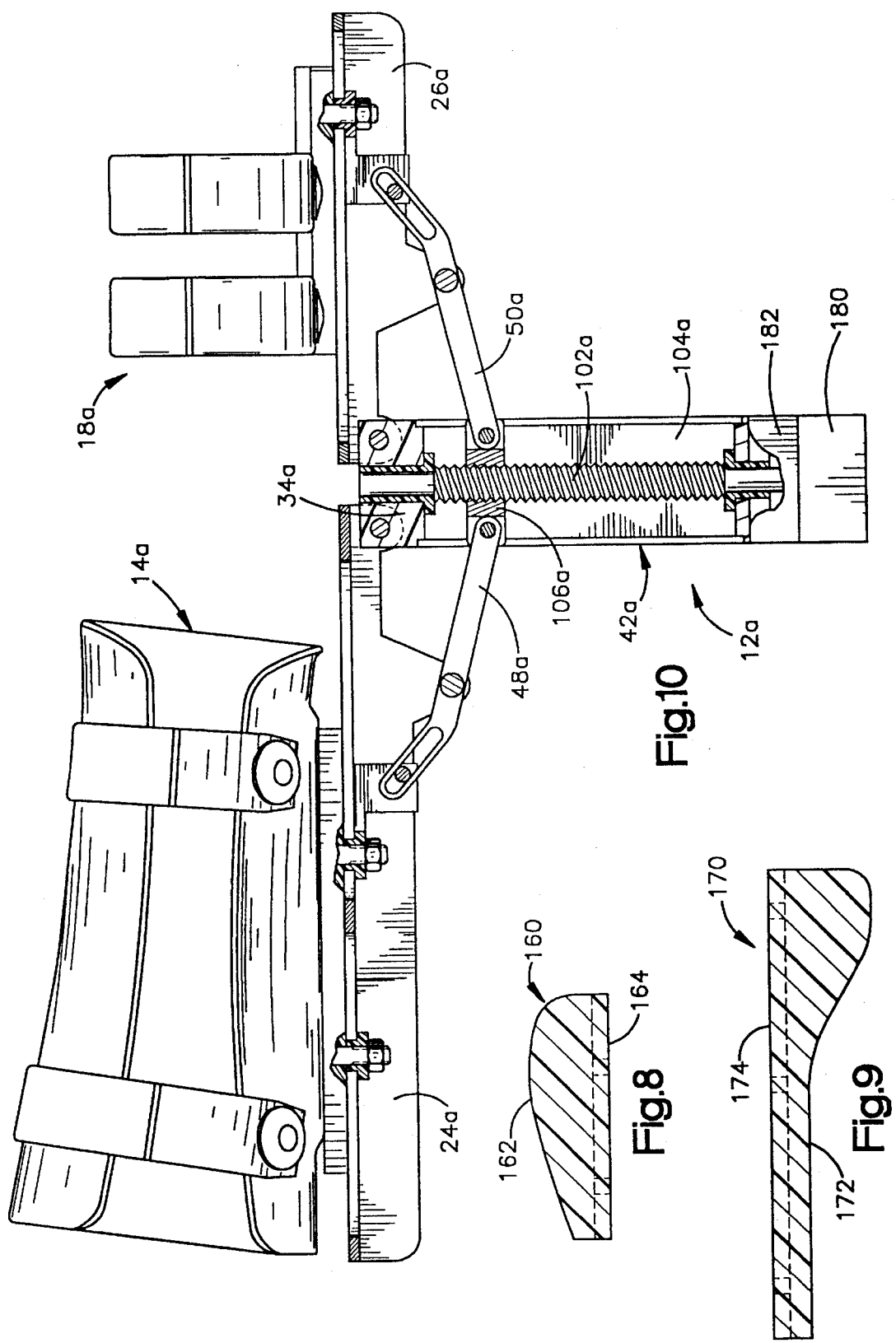

5,503,619

ORTHOSIS FOR BENDING WRISTS

RELATED APPLICATIONS

This is a continuation-in-part of application Ser. No. 08/126,081 filed Sep. 23, 1993, now U.S. Pat. No. 5,395,303. The aforementioned application Ser. No. 08/126,081 is itself a divisional of application Ser. No. 07/690,845 filed Apr. 24, 1991 (now U.S. Pat. No. 5,285,773). The aforementioned application Ser. No. 07/690,845 is itself a continuation-in-part of application Ser. No. 07/559,700 filed Jul. 30, 1990 (now U.S. Pat. No. 5,167,612). The aforementioned application Ser. No. 07/690,845 is also a continuation-in-part of application Ser. No. 07/686,811 filed Apr. 17, 1991 (now U.S. Pat. No. 5,213,094). The benefit of the earlier filing dates of the aforementioned applications Ser. Nos. 08/126,081; 07/690,845; 07/559,700 and 07/686,811 is claimed for all common subject matter.

BACKGROUND OF THE INVENTION

The present invention relates to a new and improved orthosis for use in bending wrists.

A known orthosis for use in bending wrists is disclosed in U.S. Pat. No. 4,538,595. The orthosis disclosed in this patent is operable through a range of motion of between 0 to +20 degrees of dorsal flexion and to −40 degrees of planter flexion. This known orthosis is designed for use with one arm, that is, the left arm.

SUMMARY OF THE INVENTION

The present invention provides a new and improved method for using the same orthosis to sequentially bend different wrists in flexion and extension. When the orthosis is to be used to bend a first wrist in flexion, the orthosis is mounted on a first arm with the orthosis in a first orientation relative to the first wrist. A mechanism in the orthosis is then operated to bend the wrist in flexion under the influence of force transmitted from the mechanism.

When the orthosis is to be subsequently used to bend a second wrist in extension, the orthosis is mounted on the second arm in a second orientation which is different than the first orientation. The orthosis is then operated to bend the second wrist in extension. To bend the second wrist in extension, the mechanism in the orthosis is operated in the same direction as it was previously operated in to bend the wrist in flexion.

BRIEF DESCRIPTION OF THE DRAWINGS

The foregoing and other features of the invention will become more apparent upon a consideration of the following description taken in connection with the accompanying drawings, wherein:

FIG. 8 is a somewhat schematicized sectional view of an adaptor to be mounted on a cuff of the orthosis of FIGS. 1–7 to engage the palm of a hand;

FIG. 9 is a somewhat schematicized sectional view of an adaptor to be mounted on a cuff of the orthosis of FIGS. 1–7 to engage the back of a hand; and FIG. 10 is a sectional view of an embodiment of the orthosis in which the actuator mechanism is driven by an electric motor.

DESCRIPTION OF SPECIFIC PREFERRED EMBODIMENTS OF THE INVENTION

Orthosis - General Description

Figure 1:
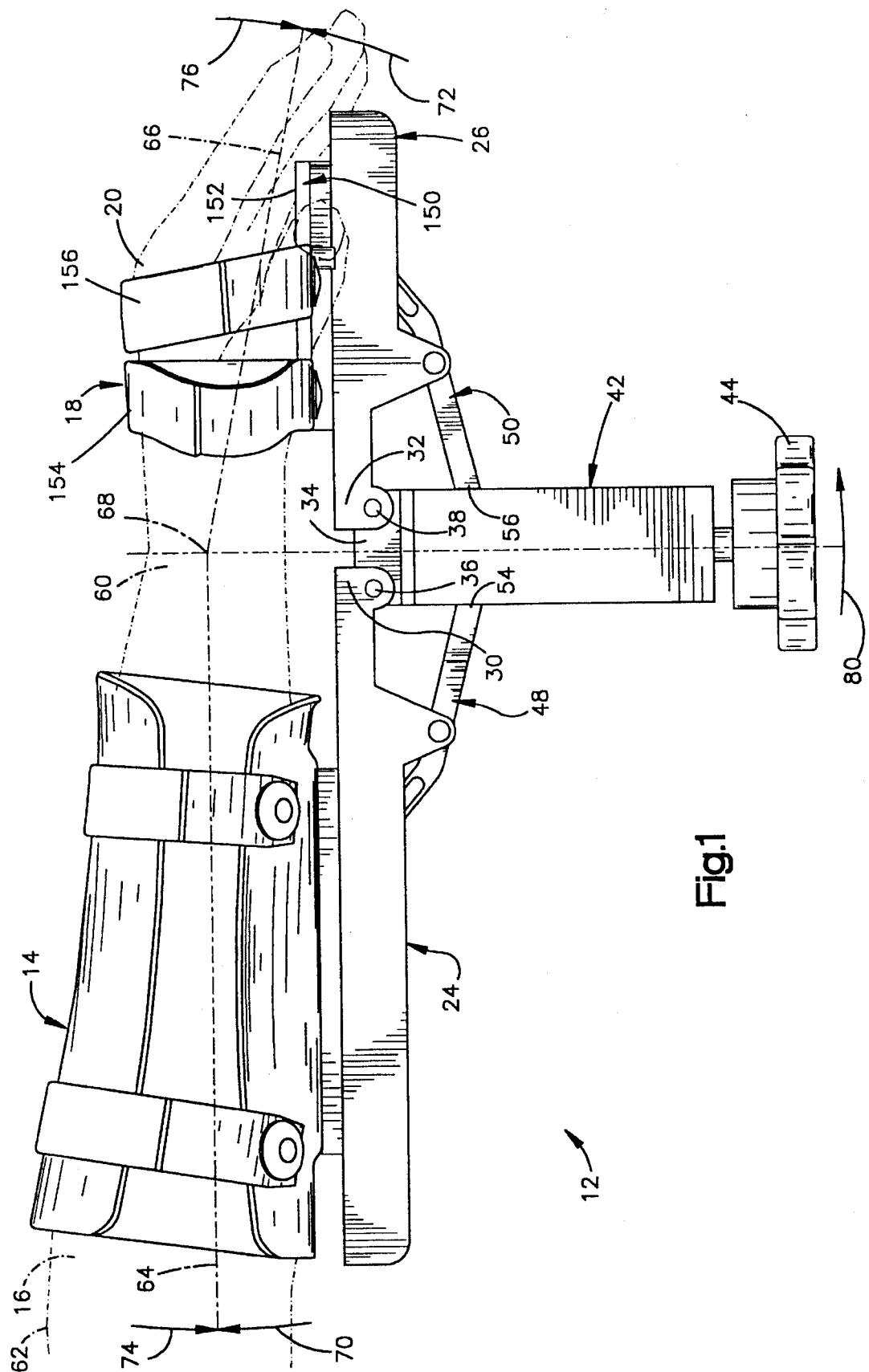
FIG. 1 is an illustration of an orthosis constructed in accordance with the present invention and mounted on a first arm in an orientation in which the orthosis can be operated to bend a first wrist in flexion.

An orthosis 12 can be used to bend one wrist in flexion and subsequently used to bend another wrist in extension. The orthosis 12 includes a first cuff 14 which is connected with a forearm 16 of a person. A second cuff 18 is connected with a hand 20 of a person. The cuffs 14 and 18 may have any desired construction as long as they are effective to engage the forearm 16 and hand 20.

A first cuff arm 24 is connected with the first cuff 14. A second cuff arm 26 is connected with the second cuff 18. End portions 30 and 32 of the linear cuff arms 24 and 26 are spaced apart from each other.

The end portions 30 and 32 of the cuff arms 24 and 26 are interconnected by a base link 34. Thus, the first cuff arm 24 is pivotally connected to the base link 34 at a pivot connection 36. The second cuff arm 26 is pivotally connected to the base link 34 at a pivot connection 38. The cuff arms 24 and 26 are pivotal about spaced apart parallel axes at the pivot connections 36 and 38.

An actuator mechanism 42 transmits force to simultaneously pivot the cuff arms 24 and 26 about the pivot connections 36 and 38 and to move the cuffs 14 and 18 along the cuff arms. The actuator mechanism 42 transmits force from an input member which, in the illustrated embodiment of the orthosis 12, is a manually rotatable knob 44. Force is transmitted from the knob 44 through the actuator mechanism 42 to drive links 48 and 50. Force is transmitted from the drive links 48 and 50 to pivot the cuff arms 24 and 26 about the pivot connections 36 and 38. In addition, force is transmitted from the drive links 48 and 50 to move the cuffs 14 and 18 along the cuff arms 24 and 26 as the cuff arms are pivoted about the pivot connections 36 and 38.

Figure 2:
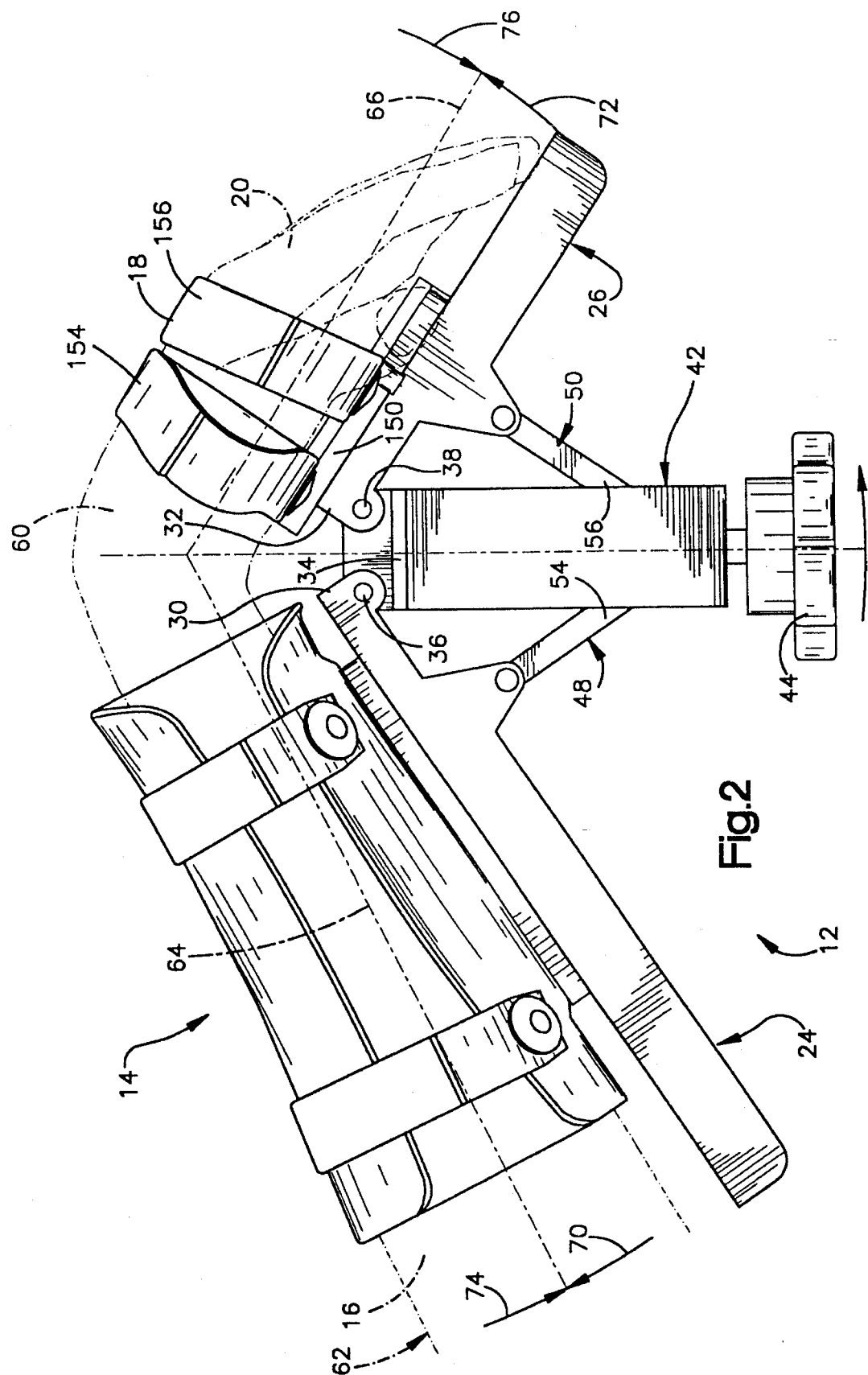
FIG. 2 is an illustration depicting the manner in which the orthosis of FIG. 1 is operated to bend the first wrist in flexion.

The actuator mechanism 42 is operable to move the cuff arms 24 and 26 from initial or aligned positions (FIG. 1) to actuated positions (FIG. 2). Operation of the actuator mechanism 42 moves inner end portions 54 and 56 of the drive links 48 and 50 downward (as viewed in FIGS. 1 and 6) away from a wrist 60 connected with the forearm 16 and hand 20. As this occurs, the cuff arms 24 and 26 are pivoted about parallel spaced apart axes which extend through the pivot connections 36 and 38 and are perpendicular to longitudinal central axes of the cuff arms 24 and 26.

As the inner end portions 54 and 56 of the drive links 48 and 50 are moved away from the wrist 60, the cuffs 14 and 18 move inward, along the cuff arms 24 and 26, toward the wrist 60 and the pivot connections 36 and 38. This inward movement of the cuffs 14 and 18 toward the wrist 60 and the pivot connections 36 and 38 reduces the amount of distraction applied to the wrist 60. This enables the wrist 60 to be bent without being distracted or compressed. Although it is advantageous to bend the wrist 60 without either compressing or distracting the soft tissue in the wrist, there is a slight controlled distraction of the soft tissue in order to be certain that compression of the wrist is avoided.

The construction of the orthosis 12 and the manner in which the actuator mechanism 42 pivots the cuff arms 24 and 26 and moves the cuffs 14 and 18 along the cuff arms 24 and 26 is generally similar to that disclosed in U.S. Pat. No. 5,285,773. The disclosure in U.S. Pat. No. 5,285,773 is incorporated herein by this reference thereto.

Bending Wrist in Flexion

When a left wrist 60 (FIG. 1) is to be bent in flexion, the first cuff 14 is connected with the left forearm 16 and the second cuff 18 is connected with the left hand 20. The cuff arms 24 and 26 are aligned with each other, that is, in a generally horizontal orientation as viewed in FIG. 1. The cuff arms 24 and 26 are disposed at the palmar side of the arm 62. Thus, the cuff arms 24 and 26 are disposed in-an inner sector having a center at the wrist 60 and radians which are coincident with longitudinal central axes of the left hand 20 and the left forearm 16.

The longitudinal central axis of the left forearm 16 has been indicated at 64 in FIG. 1 and the longitudinal central axis of the left hand 20 has been indicated at 66 in FIG. 1. The axes 64 and 66 intersect at a center 68 of the left wrist 60. The inner sector includes the arc indicated by arrows 70 and 72 in FIG. 1. The inner sector decreases in angle as the wrist 60 is bent in flexion from the initial position shown in FIG. 1 to the position shown in FIG. 2. The outer sector includes the arc indicated by the arrows 74 and 76 in FIG. 1. The outer sector increases in angle as the wrist 60 is bent in flexion from the initial position shown in FIG. 1 to the position shown in FIG. 2.

The actuator assembly 42 and the pivot connections 36 and 38 are disposed adjacent to the palm side of the wrist 60. Thus, the actuator mechanism 42 and the pivot connections 36 and 38 are disposed in the inner sector indicated by the arrows 70 and 72 in FIG. 1.

When the input knob 44 is manually rotated in the direction of the arrow 80 in FIG. 1, the actuator mechanism 42 is operated. Operation of the actuator mechanism 42 transmits force from the knob 44 to the drive links 48 and 50. The drive links 48 and 50 to pivot the cuff arms 24 and 26 from the aligned orientation shown in FIG. 1 toward the actuated orientation shown in FIG. 2 to bend the left wrist 60 in flexion.

Operation of the actuator mechanism 42 moves the inner end portions 54 and 56 of the drive links 48 and 50 away from the wrist 60, that is, downward as viewed in FIGS. 1 and 2. This pivots the first cuff arm 24 in a counterclockwise direction (as viewed in FIGS. 1 and 2) about the pivot connection 36. Simultaneously therewith, the drive link 50 pivots the second cuff arm 26 in a clockwise direction (as viewed in FIGS. 1 and 2) about the pivot connection 38. As the cuff arms 24 and 26 are pivoted in opposite directions about the pivot connections 36 and 38 toward the orientation shown in FIG. 2, the wrist 60 is bent in flexion.

During pivotal movement of the cuff arms 24 and 26 and bending of the wrist 60 in flexion, the drive links 48 and 50 transmit force from the actuator mechanism 42 to the cuffs 14 and 18 to move the cuffs along the cuff arms 24 and 26 toward the wrist 60 and the pivot connections 36 and 38. The drive links 48 and 50 are moved through the same distance by the actuator mechanism 42 and have the same configuration. Therefore, the cuffs 14 and 18 are moved along the cuff arms 24 and 26 through the same distance as the cuff arms are pivoted about the pivot connections 36 and 38.

In the illustrated embodiment of the invention, the cuff 14 is movable along the cuff arm 24 through a distance of approximately 1½ inches toward the pivot connection 36 as the orthosis 12 is operated from the initial condition of FIG. 1 to the fully actuated condition of FIG. 2. Similarly, the second cuff 18 is movable through 1½ inches along the second cuff arm 26 toward the pivot connection 38 through a distance of 1½ inches as the orthosis 12 is operated from the initial condition of FIG. 1 to the fully actuated condition of FIG. 2. It should be understood that the foregoing distance through which the cuffs 14 and 18 move has been set forth for purposes of clarity of description. It is contemplated that the cuffs 14 and 18 could be moved through distances different than the specific distance set forth herein. It should also be understood that the cuffs 14 and 18 could be moved through unequal distances if desired.

Moving the cuffs 14 and 18 toward the wrist 60 and the pivot connections 36 and 38 as the wrist is bent in flexion greatly reduces the distractive forces applied to the soft tissue in the wrist 60. The drive links 48 and 50 are designed so that there is a small amount of distractive force applied to the wrist 60. The design of the drive links 48 and 50 is such that there is no compressive force applied to the wrist 60 as it is bent in flexion from the initial condition of FIG. 1 to the condition shown in FIG. 2.

In the illustrated embodiment of the invention, the cuff arms 24 and 26 are moved by the actuator mechanism 42 through a range of movement from positions in which the cuff arms are aligned with each other (FIG. 1) to a condition of maximum flexion in which the longitudinal axes of the cuff arms are disposed at an angle of 90° relative to each other. As the orthosis 12 is operated to bend the wrist 60 in flexion, the size of the inner sector, indicated by the arrows 70 and 72 in FIGS. 1 and 2, is decreased and the size of the outer sector, indicated by the arrows 74 and 76, is increased. It should be understood that the foregoing specific range of movement for the cuffs 14 and 18 and the range of movement of the cuff arms 24 and 26 relative to each other has been set forth herein for purposes of clarity of description and it is contemplated that specific embodiments of the orthosis 12 will have cuffs 14 and 18 which move through different distances relative to each other and are movable to different angular orientations relative to each other.

It is contemplated that the specific procedure which is followed to bend the wrist 60 in flexion will vary depending upon the conditions of the wrist and the desires of a surgeon or therapist supervising the use of the orthosis 12. However, it is believed that it may be preferred to use a static progressive stretch procedure during bending of the wrist 60. This procedure is implemented by operating the actuator mechanism 42 to bend the wrist 60 in flexion to a limit of tolerance of the wrist without severe pain. This position of the wrist 60 is held for a period of time, for example, five minutes, to allow the tissue in the wrist to relax. As the tissue relaxes, stress decreases. After the period of time has elapsed, the input member 44 is manually rotated to again stretch the soft tissue in the wrist 60 to the limit of tolerance.

This condition is again held for a period of time, for example, five minutes, to allow the tissue in the wrist to again relax. The process is repeated for the duration of a therapy session which, may be approximately thirty minutes long.

The input knob 44 may be manually rotated by either the patient, that is, the person having the arm 62 on which the orthosis 12 is mounted, or by a supervisory personnel, such as a therapist. However, it is believed that it will be desired to have the patient actuate the orthosis 12 to effect bending of the wrist 60. The patient can feel when the tissue has tightened and the wrist has been bent to the limit of its tolerance, without severe pain. The patient can also feel when the tissue has relaxed and further actuation of the orthosis 12 to further bend the wrist in flexion can be undertaken.

Although the foregoing description of bending a wrist 60 in flexion with the orthosis 12 has been in conjunction with the bending of a left wrist, it should be understood that the orthosis can be equally as well used to bend a right wrist in flexion. Thus, the cuffs 14 and 18 are designed to enable them to be used to connect either a left forearm or a right forearm with the cuff arm 24 and to connect either a left hand or a right hand with the cuff arm 26.

Bending Wrist in Extension

When a wrist is to be bent in extension, the orthosis 12 is mounted on an arm of a patient in an orientation which is different than the orientation in which it is mounted on the arm of the patient to bend a wrist in flexion. When a right wrist 80 (FIG. 3) is to be bent in extension from the initial condition illustrated in FIG. 3, the first cuff 14 is connected with the right forearm 84. The second cuff 26 is connected with the right hand 86. The actuator assembly 42 is positioned adjacent to the back side of the wrist 80 and hand 86.

Figure 3:
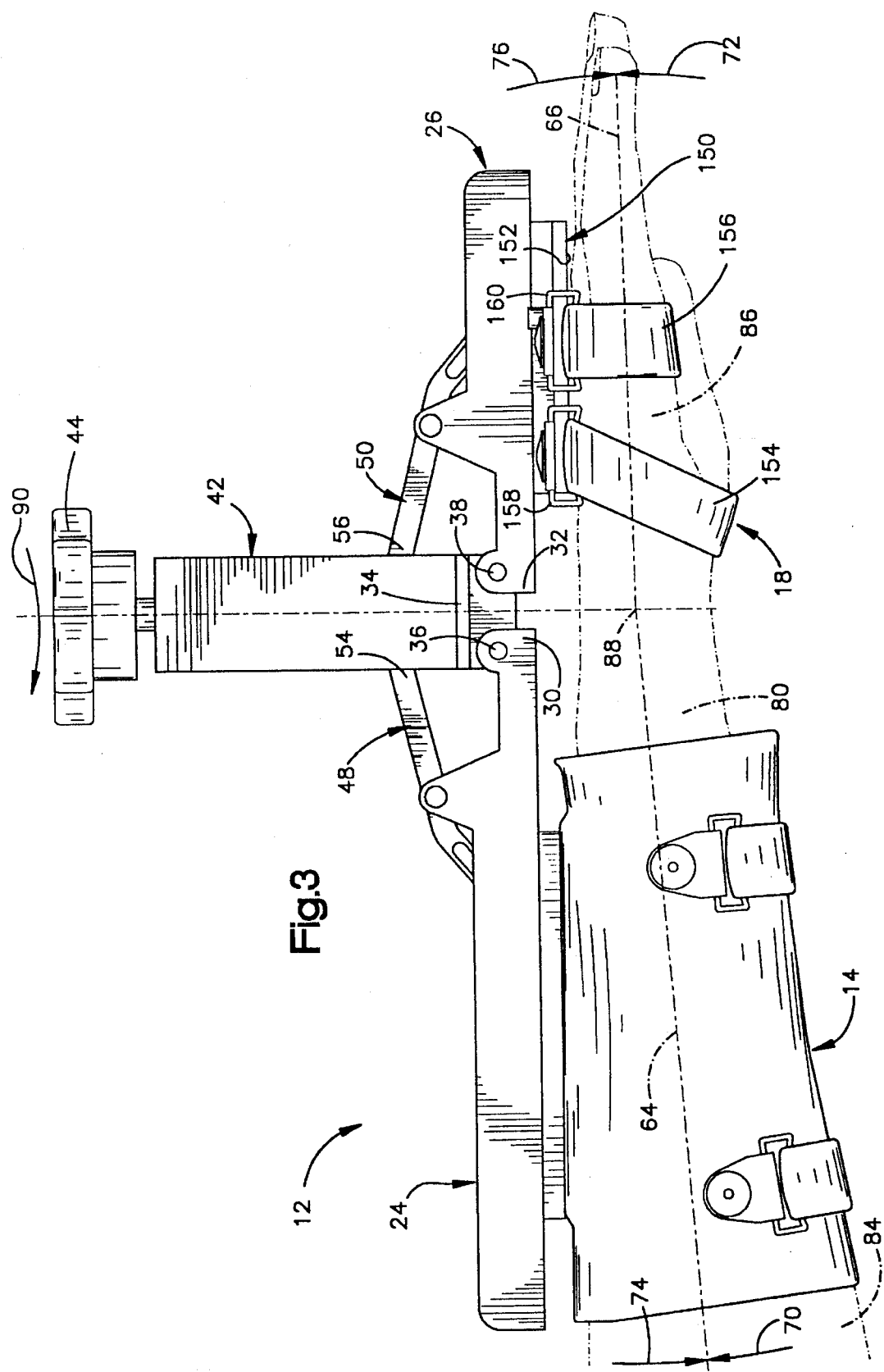
FIG. 3 is an illustration, generally similar to FIG. 1, of the orthosis mounted on a second arm in an orientation in which the orthosis can be operated to bend a second wrist in extension.

The orientation of the orthosis 12 is such that the first cuff arm 24 is in the outer sector, indicated by the arrows 74 and 76 in FIG. 3. The second cuff arm 26 is also in the outer sector. The actuator mechanism 42 is disposed in the outer sector and is aligned with a center 88 of the wrist 80.

The input knob or member 44 is manually rotated, in the direction of the arrow 90 in FIG. 3, to operate the actuator mechanism 42. Operation of the actuator mechanism 42 transmits force from the input knob 90 to the drive links 48 and 50. As the input knob 44 is manually rotated, the actuator mechanism 42 moves the inner end portions 54 and 56 of the drive links 48 and 50 away from the wrist 50. Thus, the inner end portions 54 and 56 of the drive links 48 and 50 are moved upward from the position shown in FIG. 3 toward the position shown in FIG. 4 as the input knob 44 is manually rotated.

As the end portions 54 and 56 of the drive links 48 and 50 are moved upward (as viewed in FIG. 3), the cuff arms 24 and 26 are pivoted in opposite directions about parallel axes extending through the pivot connections 36 and 38. Thus, the cuff arm 24 is pivoted in a clockwise direction (as viewed in FIG. 3) about the pivot connection 36. The cuff arm 26 is pivoted in a counterclockwise direction about the pivot connection 38.

Figure 4:
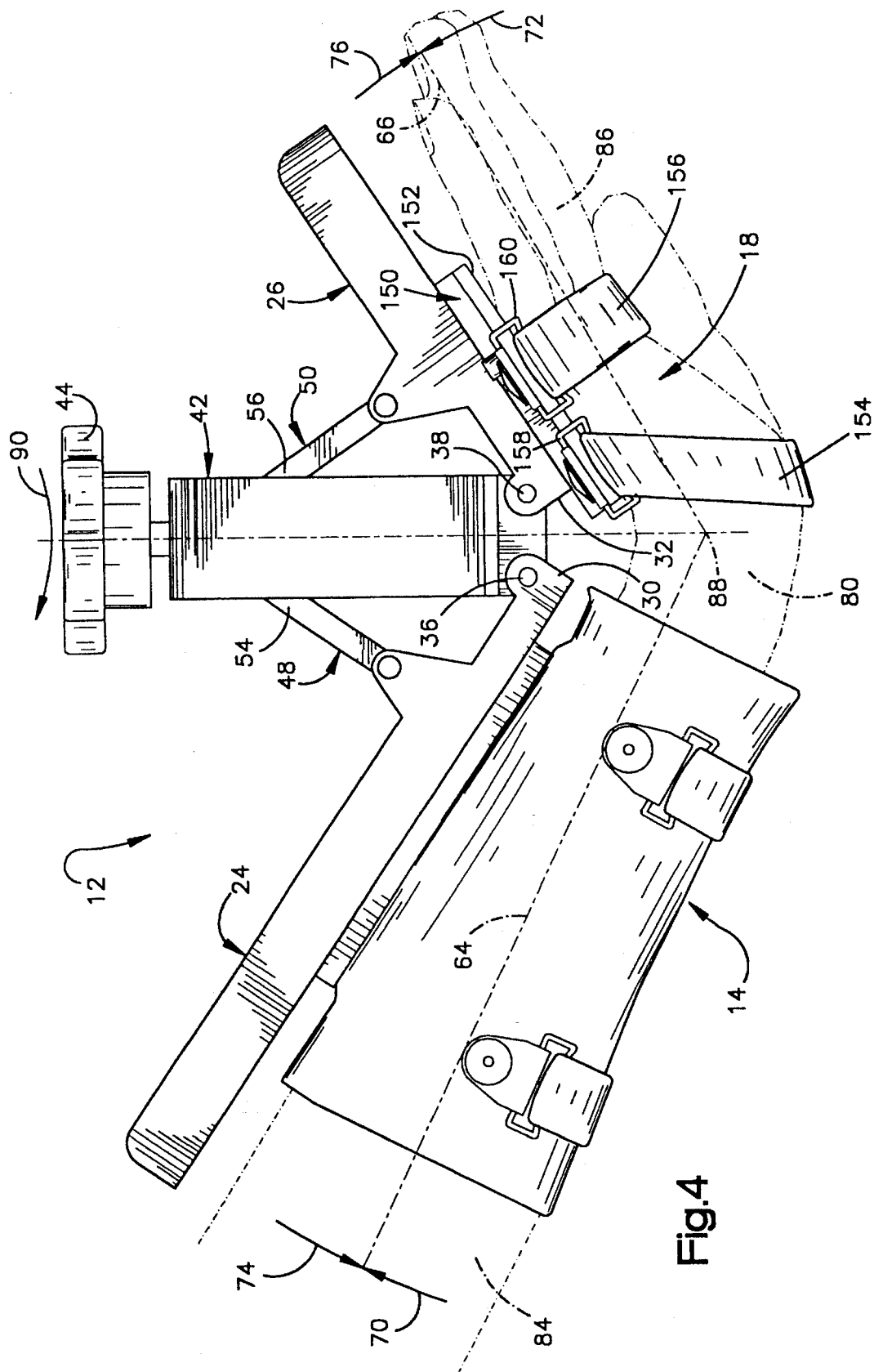
FIG. 4 is an illustration depicting the manner in which the orthosis of FIG. 3 is operated to bend the second wrist in extension.

As the cuff arms 24 and 26 are pivoted by the drive links 48 and 50, the wrist 80 is bent in extension from the initial condition shown in FIG. 3 toward the condition shown in FIG. 4. As this occurs, the outer sector, indicated by the arrows 74 and 76 in FIG. 3, decreases in size and the inner sector, indicated by the arrows 70 and 72 in FIG. 3, increases in size. The cuff arms 24 and 26 are pivoted toward the actuator mechanism 42 in the outer sector.

As the cuff arms 24 and 26 are pivoted under the influence of force transmitted from the actuator mechanism 42 through the drive links 48 and 50, the cuffs 14 and 18 are moved along the cuff arms 24 and 26. Thus, force is transmitted from the drive links 48 and 50 to the cuffs 14 and 18 to move the cuffs along the cuff arms toward the wrist 80 and the pivot connections 36 and 38. The first cuff 14 is moved along the first cuff arm 24 toward the wrist 80 and the pivot connection 36 as the first cuff arm is pivoted in a clockwise direction about the pivot connection 36. Similarly, the second cuff 18 is moved along the second cuff arm 26 toward the wrist 80 and the pivot connection 38 as the second cuff arm is pivoted in a counterclockwise direction about the pivot connection 38. Moving the cuffs 14 and 18 toward the wrist 80 and the pivot connections 36 and 38 minimizes the extent of distraction of the wrist 80 while ensuring that there is no compression of the wrist.

It is believed that a static progressive stretch procedure may be preferred for bending the wrist 80 in extension. Thus, the input knob or member 44 is manually rotated to operate the actuator mechanism 42 and effect pivoting of the cuff arms 24 and 26 to bend the wrist 80 in flexion until the patient feels tissue tightness, but not severe pain. The orthosis 12 is maintained in that position for a period of time, which may be five minutes. When the tissue relaxes, the input member or knob 44 is again rotated to stretch the tissue. The steps of operating the orthosis 12 to stretch the tissue, interrupting operation of the orthosis to allow the tissue to relax and then again operating the orthosis to again stretch the tissue is repeated for the duration of a therapy session.

As was previously mentioned, the knob or input member 44 may be manually rotated by a therapist or surgeon. However, it is believed that it will be preferred to have the patient manually rotate the knob 44. Thus, the person having the hand 86, wrist 80 and forearm 84 will rotate the knob until he or she feels the tissue tighten and will further rotate the knob 44 to further bend the wrist 80 when he or she feels the tissue relax.

Although the foregoing description has been in conjunction with the bending of a right wrist 80 in extension, it should be understood that the orthosis 12 may be used to bend a left wrist in extension. In the example of bending the wrist 80 in extension illustrated in FIGS. 3 and 4, the wrist 80 is bent from an initial straight condition illustrated in FIG. 3. However, it is believed that, under certain circumstances, the wrist may initially be in the flexed condition shown in FIG. 2 and is to be bent in extension from the flexed condition to the condition shown in FIG. 1. When this is to be done, the orthosis 12 is mounted on the arm in the same orientation shown in FIG. 2 and is operated to bend the wrist in extension toward the straight condition illustrated in FIG. 1. Thus, the cuffs 14 and 16 can be used to transmit forces which pull the wrist from a straight initial condition shown in FIGS. 1 and 3 toward a bent condition shown in FIGS. 2 or 4 or may be used to push against the forearm and hand to bend the wrist from the condition shown in FIG. 2 to the straight condition shown in FIG. 1.

Actuator Mechanism and Drive Links

Figure 5:
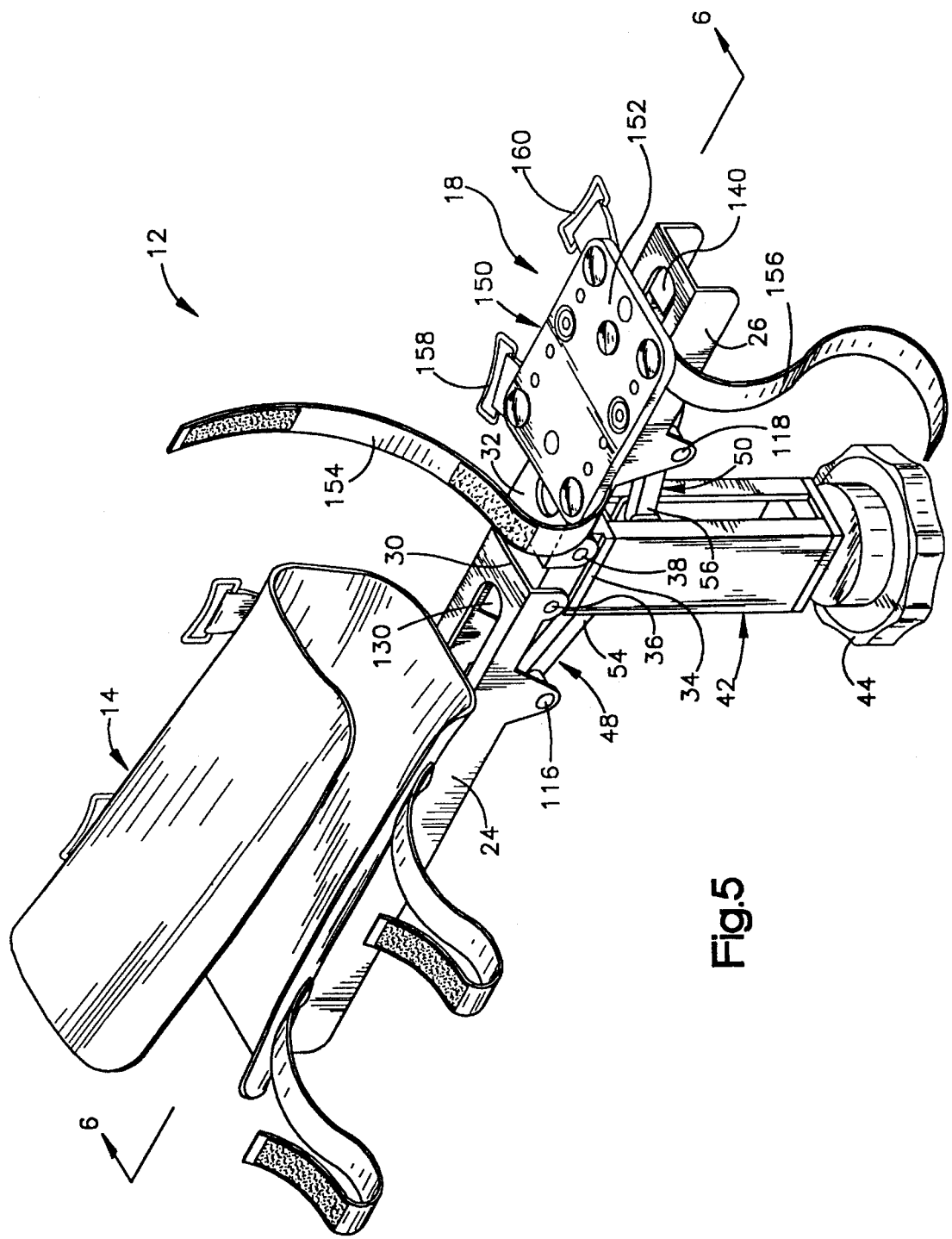
FIG. 5 is a pictorial illustration further illustrating the construction of the orthosis of FIGS. 1–4.

The actuator mechanism 42 (FIGS. 5 and 6) is supported on the base link 34. The actuator mechanism 42 includes an externally threaded member or screw 102 (FIG. 6) which is rotatably supported within a housing 104. A central axis of the screw 102 extends through the center of the base link 34 and through the center of a wrist 60 or 80 with which the orthosis 12 is connected. A central axis of the screw 102 extends midway between and is perpendicular to parallel axes extending through the pivot connections 36 and 38.

The manually rotatable knob 44 is fixedly connected to the lower (as viewed in FIG. 6) end of the screw 102. An actuator member or block 106 has internal thread convolutions which engage external thread convolutions on the screw 102. In the illustrated embodiment of the invention, the internally threaded actuator member 106 is movable along the externally threaded screw 102. However, the screw 102 could be movable relative to the actuator member 106. If this was done, the drive links 48 and 50 would be connected with the screw 102.

Upon rotation of the input member or knob 44, the actuator member 106 is moved away from the base link 34 toward the input member or knob 44. As this occurs, the drive links 48 and 50 pivot the cuff arms 24 and 26 about the pivot connections 36 and 38. Of course, pivotal movement of the cuff arms 24 and 26 bends a wrist 60 or 80 with which the orthosis 12 is connected. When the orthosis 12 is mounted in the orientation shown in FIGS. 1 and 2, downward movement of the actuator member 106 away from the wrist 60 and base link 34 bends the wrist in flexion. When the orthosis 12 is mounted in the orientation shown in FIGS. 3 and 4, upward movement of the actuator member 106 away from the wrist 80 and base link, 34 bends the wrist in extension.

The actuator member 106 is moved away from the base link 34 to effect operation of the orthosis 12 from the initial condition shown in FIGS. 1 and 3 to the actuated condition shown in FIGS. 2 and 4. The actuator member 106 moves along a linear path which extends perpendicular to the parallel axes through the pivot connections 36 and 38. The path along which the actuator member 106 moves has a longitudinal central axis which is coincident to the central axis of the screw 102 and extends between the end portions 30 and 32 of the cuff arms 24 and 26.

The input member or knob 44 is manually rotated in the same direction to bend the wrist 60 in flexion from the initial condition of FIG. 1 to the condition shown in FIG. 2 and to bend the wrist 80 in extension from the initial condition of FIG. 3 to the condition shown in FIG. 4. In the illustrated embodiment of the invention, the screw 102 has a right hand thread so that the knob 44 is manually rotated in a clockwise direction to operate the actuator mechanism 42 when the orthosis 12 is disposed in the inner sector (FIG. 1) or in the outer sector (FIG. 3). It should be understood that an input member other than the knob 44 could be used to operate the actuator mechanism 42 if desired.

Figure 6:
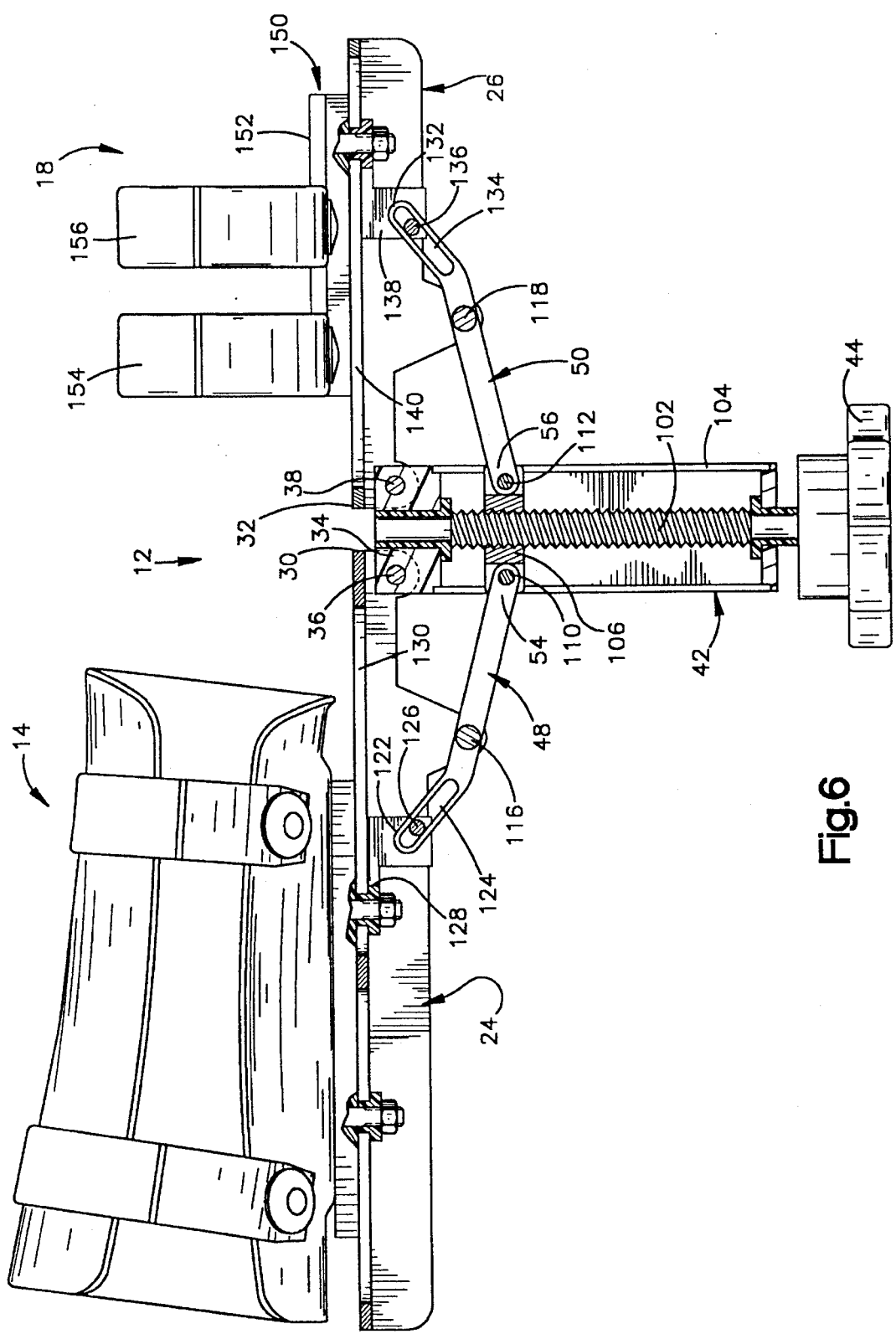
FIG. 6 is a sectional view, taken generally along the line 6–6 of FIG. 5, illustrating the construction of an actuator mechanism in the orthosis.
Figure 7:
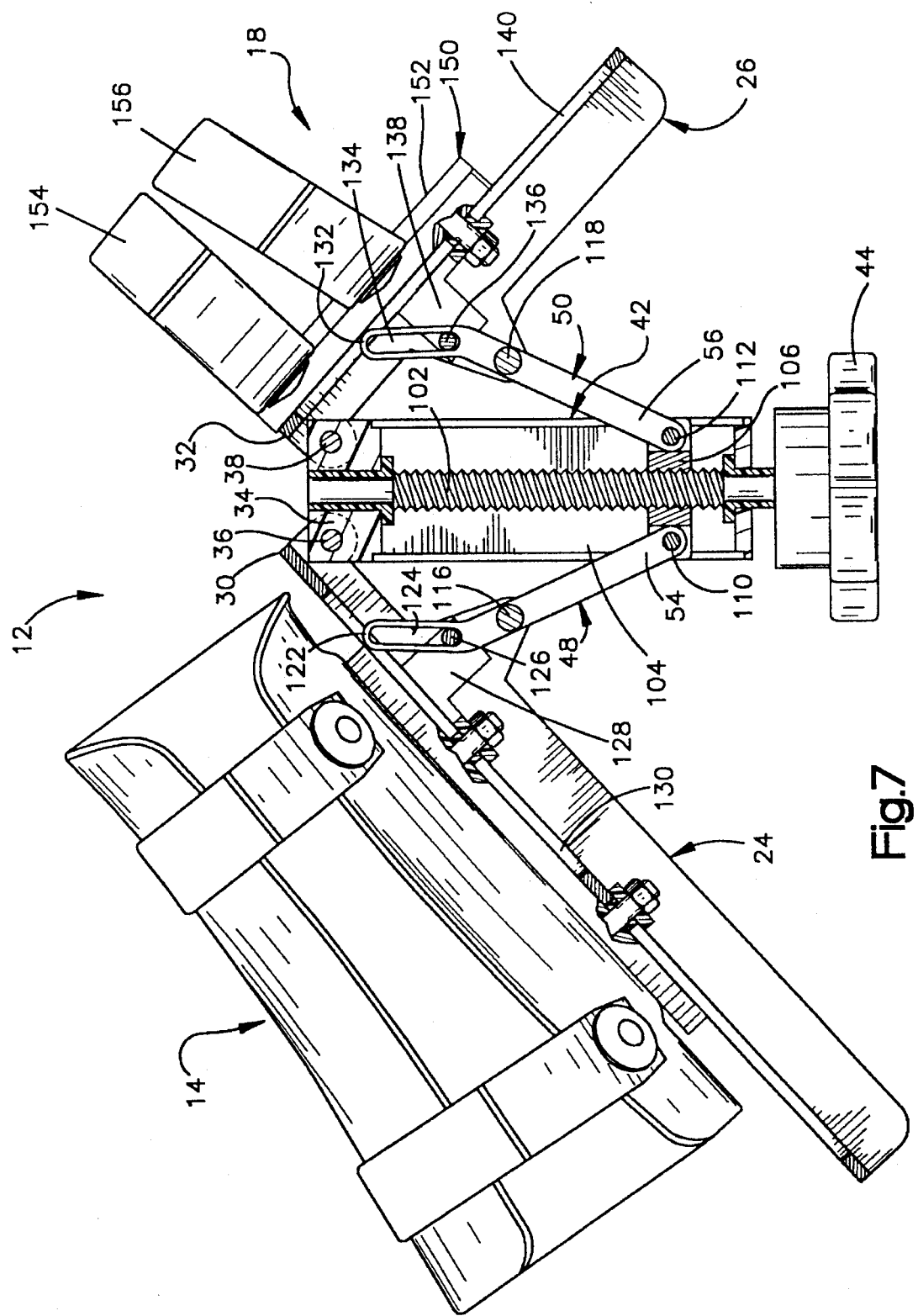
FIG. 7 is a sectional view, generally similar to FIG. 6, illustrating the manner in which the orthosis is operated to bend a wrist.

The drive links 48 and 50 are pivotally connected with the actuator member 106 at pivot connections 110 and 112 (FIGS. 6 and 7). The drive link 48 is pivotally connected with the cuff arm 24 at a pivot connection 116. The drive link 50 is pivotally connected with the cuff arm 26 at the pivot connection 118.

An outer end portion 122 of the drive link 48 has a slot 124. A pin 126 extends through the slot 124 and connects the outer end portion 122 of the drive link 48 with a cuff actuator block 128 which is fixedly connected with the cuff 14. The actuator block 128 is movable along a slot 130 in the cuff arm 24.

Similarly, an outer end portion 132 of the drive link 50 has a slot 134. A pin 136 extends through the slot 134 and connects the outer end portion 132 of the drive link 50 with an actuator block 138 which is connected with the cuff 18. The actuator block 138 is movable along a slot 140 in the cuff arm 26.

Upon manual rotation of the input member or knob 44 in a clockwise direction, the screw 102 is rotated to move the actuator member 106 downward (as viewed in FIG. 6) away from the base link 34. As this occurs, the drive link 48 is pivoted in a clockwise direction about the pivot connection 110 and transmits force to the pivot connection 116 between the drive link 48 and cuff arm 24. The force transmitted from the drive link 48 to the cuff arm 24 at the pivot connection 116 pivots the cuff arm 24 in a counterclockwise direction about an axis extending through the pivot connection 36 in a direction perpendicular to a longitudinal central axis of the cuff arm 24. This results in the cuff arm 24 pivoting from the initial position shown in FIG. 6 to the fully actuated position shown in FIG. 7 as the actuator member 106 moves downward along the screw 102.

As the drive link 48 pivots about the connection 116 with the cuff arm 24, the outer end portion 122 of the drive link is pivoted in a clockwise direction about the pivot connection 116. This results in the outer end portion 122 of the drive link 48 moving the actuator block 128 along the cuff arm 24 toward the pivot connection 36. The actuator block 128 is moved along the cuff arm 24 under the influence of force transmitted from the side surfaces of the slot 124 through the pin 126 to the actuator block.

As the cuff arm 24 is being pivoted and the cuff 14 is being moved along the cuff arm 24 by the drive link 48, the drive link 50 pivots the cuff arm 26 and moves the cuff 18 along the cuff arm 26. Thus, as the actuator member 106 moves downward along the screw 102 from the position shown in FIG. 6 to the position shown in FIG. 7, the drive link 50 is pivoted in a counterclockwise direction about the pivot connection 112. As this occurs, force is transmitted from the drive link 50 through the pivot connection 118 to the cuff arm 26 to pivot the cuff arm in a clockwise direction about an axis extending through the pivot connection 38. The axis about which the cuff arm 26 pivots extends perpendicular to a longitudinal central axis of the cuff arm 26 and parallel to the axis about which the cuff arm 24 pivots.

As the cuff arm 26 pivots about the pivot connection 38, the drive link 50 pivots in a counterclockwise direction relative to the cuff arm 26 about the pivot connection 118. This results in the cuff actuator block 138 being moved toward the pivot connection 38 by the interaction between the slot 134 and the pin 136. Thus, the cuff arms 24 and 26 are simultaneously pivoted about the pivot connections 36 and 38 by rotation of the knob 44. In addition, the cuffs 14 and 18 are simultaneously moved along the cuff arms by rotation of the knob 44.

In the illustrated embodiment of the invention, the drive links 48 and 50 have the same configuration and were operable to move the cuffs 14 and 18 through the same distance along the cuff arms 24 and 26. Thus, in one specific embodiment of the orthosis 12, the cuff 14 was moved through 1½ inches along the cuff arm 24 and the cuff 18 was moved through 1½ inches along the cuff arm 26 as the actuator member 106 moved along the screw 102 from the position illustrated in FIG. 6 to the position illustrated in FIG. 7. As this occurred, the cuff arm 24 was pivoted through 45° about the pivot connection 36 and the cuff arm 26 was pivoted through 45° about the pivot connection 38. In this particular embodiment of the invention, the distance between the pivot connection 110 and the pivot connection 116 to the drive link 48 and the distance between the pivot connection 112 and the pivot connection 118 to the drive link 50 was approximately 1½ inches. The distance between the pivot connection 116 and the outer end of the drive link 48 and between the pivot connection 118 and the outer end of the drive link 50 was approximately 1¼ inches.

It should be understood that the foregoing specific dimensions for the orthosis 12 and ranges of operation have been set forth herein for purposes of clarity of description. It is contemplated that the orthosis 12 will be constructed with different dimensions and different ranges of operation.

The manner in which the drive links 48 and 50 cooperate with the cuffs 14 and 18 and the manner in which the screw 102 cooperates with the actuator member 106 is similar to the disclosure in the previously mentioned U.S. Pat. No. 5,285,773. It should be understood that the specific construction of the drive links 48 and 50 and the actuator mechanism 42 could be different from the construction illustrated herein. For example, the actuator member 106 could be moved away from the base link 34 by a mechanism other than the internally and externally threaded members 102 and 106.

Cuff Adaptors

The cuff 18 includes a rectangular platform 150 (FIG. 5) having a flat upper side surface 152. The flat upper side surface 152 of the platform 150 can be placed in engagement with the palm of a hand (FIGS. 1 and 2) or the back of a hand (FIGS. 3 and 4). Suitable straps 154 and 156 extend through retainers 158 and 160 (FIG. 5) to secure the platform 150 with a hand.

It is contemplated that under certain conditions it may be desirable to have the platform 150 configured so as to have a surface which conforms to the palm of a patient's hand or to the back of a patient's hand. When the cuff 18 is to engage the palm of a patient's hand (FIGS. 1 and 2), an adaptor 160 (FIG. 8) is constructed. The adaptor 160 has an outer side surface 162 having a configuration corresponding to the configuration of the palm of a patient's hand. The adaptor 160 has a flat side surface 164 which engages the flat side surface 152 on the platform 150 (FIGS. 5 and 6) when the adaptor is connected with the platform.

The adaptor 160 is formed by molding a suitable material to have the desired configuration. Thus, a body of polymeric material is pressed against the palm of a patient's hand to mold the material to the configuration of the hand. The molded material is then hardened to form the surface 162 of the adaptor 160. A flat bottom side surface 164 of the adaptor is then connected with the platform 150 by fasteners which extend through suitable openings formed in the platform.

When the cuff 18 is to engage the back of a patient's hand (FIGS. 3 and 4), an adaptor 170 (FIG. 9) is constructed. The adaptor 170 has a side surface 172 with a configuration which corresponds to the configuration of the back of a patient's hand. The adaptor 170 is formed in the same manner as the adaptor 160. Thus, a body of polymeric material is pressed against the back of the patient's hand to mold the surface 172 with a configuration corresponding to the configuration of the patient's hand. A flat side surface 174 of the adaptor 170 is then connected with the platform 150 by suitable fasteners.

Motor Drive System

In the embodiment of the invention illustrated in FIGS. 1–7, the input member or knob 44 is manually rotated to operate the actuator mechanism 42 to transmit force from the knob 44 through the drive links 48 and 50 to the cuff arms 24 and 26 and cuffs 14 and 18. In the embodiment of the invention illustrated in FIG. 10, a motor is provided to operate the actuator mechanism. Since the embodiment of the invention illustrated in FIG. 10 is generally similar to the embodiment of the invention illustrated in FIGS. 1– 7, similar numerals will be utilized to designate similar components, the suffix letter "a" being associated with the components of the embodiment of the invention illustrated in FIG. 10 to avoid confusion.

In the embodiment of the invention illustrated in FIG. 10, cuffs 14a and 18a are connected with cuff arms 24a and 26a. The cuff arms 24a and 26a are pivotally connected to a base link 34a. Drive links 48a and 50a transmit force from an actuator mechanism 42a to the cuff arms 24a and 26a to effect pivotal movement of the cuff arms relative to a base link 34a. In addition, force is transmitted from the drive links 48a and 50a to the cuffs 14a and 18a to effect movement of the cuffs along cuff arms 24a and 26a.

The actuator mechanism 42a includes a screw or externally threaded member 102a which is rotatable relative to the base link 34a and a housing 104a. Upon rotation of the screw 102a, an internally threaded actuator member 106a is movable along the screw 102a.

In the embodiment of the invention illustrated in FIG. 10, a reversible motor 180 is connected with the screw 102a through a gear box 182. Although a pneumatic motor could be utilized, the motor 180 is an electric motor. Suitable controls (not shown) are actuatable either by a patient or a therapist to effect operation of the electric motor 180 in either a forward or reverse direction. Upon operation of the motor 180, the gear box 182 transmits force from the motor to the screw 102a. This force rotates the screw 102a to move the actuator member 106a along the screw.

It is contemplated that suitable controls may be provided in association with the electric motor 180 to effect a cyclical operation of the motor in forward and reverse directions. Thus, the motor 80 is operated in a forward direction to move the actuator member 106a downward along the screw 102a and then is operated in a reverse direction to effect movement of the actuator member 106a in an upward direction along the screw 102a. This cyclical operation of the motor 180 may be repeated without interruption to provide the orthosis 12a with a constant passive motion mode of operation. Although only an electric motor 180 has been shown in FIG. 10, it is contemplated that a manually operated input member could be associated with the motor 180 and screw 102a in the same manner as is disclosed in U.S. Pat. No. 5,285,773, the disclosure of which has been and hereby is incorporated herein.

Conclusion

The present invention provides a new and improved method for using the same orthosis 12 to sequentially bend wrists 60 and 80 in flexion and extension. When the orthosis 12 is to be used to bend a first wrist 60 in flexion, the orthosis is mounted on a first arm with the orthosis in a first orientation (FIG. 1) relative to the first wrist 60. A mechanism 42 in the orthosis 12 is then operated to bend the wrist 60 in flexion under the influence of force transmitted from the mechanism.

When the orthosis 12 is to be subsequently used to bend a second wrist 80 in extension, the orthosis is mounted on the second arm in the second orientation (FIG. 3) which is different than the first orientation. The orthosis 12 is then operated to bend the second wrist 80 in extension. To bend the second wrist 80 in extension, the mechanism 42 in the orthosis is operated in the same direction as it was previously operated in to bend the wrist in flexion.

Having described the invention, the following is claimed:

1. A method of using the same orthosis to sequentially bend different wrists, said method comprising the steps of mounting the orthosis on a first arm with the orthosis in a first orientation relative to a first wrist, bending the first wrist in flexion by operating a mechanism in the orthosis in a first direction while the orthosis is mounted on the first arm in the first orientation, mounting the orthosis on a second arm with the orthosis in a second orientation relative to a second wrist, said second orientation being different than the first orientation, and bending the second wrist in extension by operating the mechanism in the orthosis in the first direction while the orthosis is mounted on the second arm in the second orientation.

2. A method as set forth in claim 1 wherein said step of mounting the orthosis on the first arm includes connecting a first cuff of the orthosis with a first forearm and connecting a second cuff of the orthosis with a first hand, said step of mounting the orthosis on the second arm includes connecting the first cuff of the orthosis with a second forearm and connecting a second cuff of the orthosis with a second hand.

3. A method as set forth in claim 2 wherein said step of bending the first wrist in flexion includes transmitting force from a first portion of the second cuff to a back side surface of the first hand, said step of bending the second wrist in extension includes transmitting force from the first portion of the second cuff to a palm side of the second hand.

4. A method as set forth in claim 1 wherein said step of operating the mechanism in the orthosis in a first direction while the orthosis is mounted on the first arm in the first orientation is performed by the person having the first arm, said step of operating the mechanism in the orthosis in the first direction while the orthosis is mounted on the second arm in the second orientation is performed by the person having the second arm.

5. A method as set forth in claim 1 wherein said step of operating a mechanism in the orthosis in a first direction while the orthosis is mounted on the first arm in the first orientation includes manually rotating an input member in a first direction relative to the orthosis, said step of operating a mechanism in the orthosis in a first direction while the orthosis is mounted on the second arm in the second orientation includes manually rotating an input member in the first direction relative to the orthosis.

6. A method as set forth in claim 1 wherein said step of bending the first wrist in flexion by operating the mechanism in the orthosis in the first direction includes operating the mechanism in the orthosis in the first direction to bend the first wrist in flexion in a direction away from an initial condition of the first wrist, interrupting operation of the mechanism in the orthosis for a period of time, and, thereafter, resuming operation of the mechanism in the orthosis in the first direction to resume bending of the wrist in flexion in the direction away from the initial condition, said step of bending the second wrist in extension by operating the mechanism in the orthosis in the first direction includes operating the mechanism in the orthosis in the first direction to bend the second wrist in extension in a direction away from an initial condition of the second wrist, interrupting operation of the mechanism in the orthosis for a period of time, and, thereafter, resuming operation of the mechanism in the orthosis in the first direction to resume bending of the second wrist in extension in the direction away from the initial condition of the second wrist.

7. A method as set forth in claim 1 wherein said step of bending the first wrist in flexion by operating a mechanism in the orthosis in the first direction includes moving an actuator member in the mechanism in a direction away from the first wrist, said step of bending the second wrist in extension by operating a mechanism in the orthosis in the first direction includes moving the actuator member in the mechanism in a direction away from the second wrist.

8. A method as set forth in claim 1 wherein the first wrist, a hand connected with the first wrist, and a forearm connected with the first wrist define an inner sector which decreases in angle as the first wrist is bent in flexion, the mechanism in the orthosis being disposed in the inner sector when the orthosis is mounted on the first arm in the first orientation, and wherein the second wrist, a hand connected with the second wrist, and a forearm connected with the second wrist define an outer sector which decreases in angle as the second wrist is bent in extension, the mechanism in the orthosis being disposed in the outer sector when the orthosis is mounted on the second arm in the second orientation.

9. A method as set forth in claim 1 wherein the first wrist, a hand connected with the first wrist and a forearm connected with the first wrist define an inner sector which decreases in angle as the first wrist is bent in flexion and an outer sector which increases in angle as the first wrist is bent in flexion, the mechanism in the orthosis being disposed in a first one of the inner and outer sectors when the orthosis is mounted on the first arm in the first orientation, and wherein the second wrist, a hand connected with the second wrist and a forearm connected with the second wrist define an inner sector which increases in angle as the second wrist is bent in extension and an outer sector which decreases in angle as the second wrist is bent in extension, the mechanism in the orthosis being disposed in a second one of the inner and outer sectors when the orthosis is mounted on the second arm in the second orientation.

10. A method as set forth in claim 1 wherein said step of mounting the orthosis on the first arm with the orthosis in a first orientation relative to a first wrist includes connecting a first cuff and a first cuff arm with a first forearm and connecting a second cuff and a second cuff arm with a first hand, said step of bending the first wrist in flexion includes moving one of the first and second cuffs along one of the first and second cuff arms, said step of mounting the orthosis on the second arm with the orthosis in a second orientation relative to the second wrist includes connecting the first cuff and the first cuff arm with a second forearm and connecting the second cuff and the second cuff arm with a second hand, said step of bending the second wrist in extension includes moving said one of the first and second cuffs along said one of the first and second cuff arms.

11. A method as set forth in claim 10 wherein said step of moving said one of the first and second cuffs along said one of the first and second cuff arms toward the first wrist includes transmitting force from the mechanism in the orthosis to said one of the first and second cuffs to move said one of the first and second cuffs along said one of the first and second cuff arms under the influence of force transmitted from the mechanism to said one of the first and second cuffs during bending of the first wrist in flexion, said step of moving said one of the first and second cuffs along said one of the first and second cuff arms toward the second wrist includes transmitting force from the mechanism in the orthosis to said one of the first and second cuffs to move said one of the first and second cuffs along said one of the first and second cuff arms under the influence of force transmitted from the mechanism to said one of the first and second cuffs during bending of the second wrist in extension.

12. A method as set forth in claim 11 wherein said step of moving said one of the first and second cuffs along one of the first and second cuff arms during bending of the first wrist in flexion includes moving said one of the first and second cuffs toward the first wrist, said step of moving said one of the first and second cuffs along one of the first and second cuff arms during bending of the second wrist in extension includes moving said one of the first and second cuffs toward the second wrist.

13. A method as set forth in claim 1 wherein said step of mounting the orthosis on a first arm with the orthosis in a first orientation relative to the first wrist includes connecting a first cuff and a first cuff arm with a first forearm and a second cuff and a second cuff arm with a first hand, said step of bending the first wrist in flexion includes moving the first cuff along the first cuff arm and simultaneously therewith moving the second cuff along the second cuff arm, said step of mounting the orthosis on a second arm with the orthosis in a second orientation relative to the second wrist includes connecting the first cuff and the first cuff arm with a second forearm and the second cuff and the second cuff arm with a second hand, said step of bending the second wrist in extension includes moving the first cuff along the first cuff arm and simultaneously therewith moving the second cuff along the second cuff arm.

14. A method as set forth in claim 13 wherein said steps of moving the first cuff along the first cuff arm and simultaneously therewith moving the second cuff along the second cuff arm during bending of the first wrist in flexion includes moving the first and second cuffs toward the first wrist under the influence of force transmitted to the first and second cuffs from the mechanism in the orthosis, said steps of moving the first cuff along the first cuff arm and simultaneously therewith moving the second cuff along the second cuff arm during bending of the second wrist in extension includes moving the first and second cuffs toward the second wrist under the influence of force transmitted to the first and second cuffs from the mechanism in the orthosis.

15. A method as set forth in claim 1 wherein said step of mounting the orthosis on a first arm with the orthosis in a first orientation relative to the first wrist includes connecting a first cuff and a first cuff arm with a first forearm and connecting a second cuff and a second cuff arm with a first hand, said step of bending the first wrist in flexion includes transmitting force from the mechanism in the orthosis to the second cuff arm to pivot the second cuff arm about an axis which is offset from the first wrist on a side of the first wrist toward which a palm of the first hand faces, said step of mounting the orthosis on a second arm with the orthosis in a second orientation relative to the second wrist includes connecting the first cuff and the first cuff arm with a second forearm and connecting the second cuff and the second cuff arm with a second hand, said step of bending the second wrist in extension includes transmitting force from the mechanism in the orthosis to the second cuff arm to pivot the second cuff arm about an axis which is offset from the second wrist on a side of the second wrist toward which a back of the second hand faces.

16. A method as set forth in claim 15 wherein said step of bending the first wrist in flexion includes transmitting force from the mechanism in the orthosis to the first cuff arm to pivot the first cuff arm about an axis which is offset from the first wrist on a side of the first wrist toward which the palm of the first hand faces, said step of bending the second wrist in extension includes transmitting force from the mechanism in the orthosis to the first cuff arm to pivot the first cuff arm about an axis which is offset from the second wrist on a side of the second wrist toward which the back of the second hand faces.

17. A method as set forth in claim 16 wherein said step of bending the first wrist in flexion includes transmitting force from the mechanism in the orthosis to the first and second cuffs to simultaneously move the first and second cuff arms toward the first wrist, said step of bending the second wrist in extension includes transmitting force from the mechanism in the orthosis to the first and second cuffs to simultaneously move the first and second cuffs along the first and second cuff arms toward the second wrist.

18. A method as set forth in claim 15 wherein said step of bending the first wrist in flexion includes transmitting force from the mechanism in the orthosis to the second cuff to move the second cuff along the second cuff arm, said step of bending the second wrist in extension including transmitting force from the mechanism in the orthosis to move the second cuff along the second cuff arm.

19. A method as set forth in claim 1 wherein said step of operating the mechanism in the orthosis to bend the first wrist in flexion includes moving an actuator member disposed in the mechanism away from the first wrist along a path which extends through the first wrist, said step of operating the mechanism in the orthosis to bend the second wrist in extension includes moving the actuator member disposed in the mechanism away from the second wrist along a path which extends through the second wrist.

20. A method as set forth in claim 19 wherein said steps of operating the mechanism in the orthosis include effecting relative rotation between internally and externally threaded members to move one of the threaded members connected with the actuator member relative to the other threaded member.

21. A method as set forth in claim 1 further including forming an adapter having a first side surface with a configuration corresponding to the configuration of a palm of a first hand connected with the first wrist, and mounting the adapter on a portion of the orthosis, said step of mounting the orthosis on the first arm includes connecting a first cuff of the orthosis with a first forearm connected with the first wrist and connecting a second cuff on the orthosis with the first hand with the first side surface of the adapter in engagement with the palm of the first hand.

22. A method as set forth in claim 1 further including forming an adapter having a first side surface with a configuration corresponding to the configuration of a second hand connected with the second wrist, and mounting the adapter on a portion of the orthosis, said step of mounting the orthosis on the second arm including connecting a first cuff of the orthosis with a second forearm connected with the second wrist and connecting a second cuff on the orthosis with the second hand with the first side surface of the adapter in engagement with the back of the second hand.

23. A method as set forth in claim 1 wherein said step of operating the mechanism in the orthosis in a first direction includes operating a motor to effect the transmittal of force from the motor to the mechanism.

24. A method as set forth in claim 1 wherein the first wrist, a hand connected with the first wrist, and a forearm connected with the first wrist define an inner sector which decreases in angle as the first wrist is bent in flexion, said step of bending the first wrist in flexion includes transmitting force from the mechanism in the orthosis to the second cuff to pivot the second cuff about an axis which is disposed in the inner sector, and wherein the second wrist, a hand connected with the second wrist, and a forearm connected with the second wrist define an outer sector which decreases in angle as the second wrist is bent in extension, said step of bending the second wrist in extension includes transmitting force from the mechanism in the orthosis to the second cuff to pivot the second cuff about an axis which is disposed in the outer sector.

25. A method as set forth in claim 24 wherein the mechanism in the orthosis is disposed in the inner sector when the orthosis is mounted on the first arm in the first orientation and the mechanism in the orthosis is disposed in the outer sector when the orthosis is mounted on the second arm in the second orientation.

26. A method as set forth in claim 1 wherein the first wrist, a hand connected with the first wrist, and a forearm connected with the first wrist define an inner sector which decreases in angle as the first wrist is bent in flexion, said step of bending the first wrist in flexion includes transmitting force from the mechanism in the orthosis to the first cuff to pivot the first cuff about a first axis which is disposed in the inner sector and transmitting force from the mechanism in the orthosis to the second cuff to pivot the second cuff about a second axis which is disposed in the inner sector and is spaced from the first axis, and wherein the second wrist, a hand connected with the second wrist, and a forearm connected with the second wrist define an outer sector which decreases in angle as the second wrist is bent in extension, said step of bending the second wrist in extension includes transmitting force from the mechanism in the orthosis to the first cuff to pivot the first cuff about a third axis which is disposed in the outer sector and transmitting force from the mechanism in the orthosis to the second cuff to pivot the second cuff about a fourth axis which is disposed in the outer sector and is spaced from the third axis.

27. A method as set forth in claim 26 wherein the mechanism in the orthosis is disposed in the inner sector when the orthosis is mounted on the first arm in the first orientation and the mechanism in the orthosis is disposed in the outer sector when the orthosis is mounted on the second arm in the second orientation.

28. A method as set forth in claim 26 wherein said step of bending the first wrist in flexion includes effecting relative rotation between internally and externally threaded members about an axis which extends between the first and second axes, said step of bending the second wrist in extension includes effecting relative rotation between internally and externally threaded members about an axis which extends between the third and fourth axes.

29. A method as set forth in claim 26 wherein said step of operating a mechanism in the orthosis in a first direction while the orthosis is mounted on the first arm in the first orientation includes manually rotating an input member about an axis which extends between the first and second axes, said step of operating a mechanism in the orthosis in a second direction while the orthosis is mounted on the second arm in the second orientation includes manually rotating the input member about an axis which extends between the third and fourth axes.

30. A method as set forth in claim 29 wherein said step of manually rotating an input member about an axis which extends between the first and second axes is performed by the person having the first arm, said step of manually rotating the input member about an axis which extends between the third and fourth axes is performed by the person having the second arm.

31. A method of using an orthosis to bend a wrist, said method comprising the steps of connecting a first cuff and a first cuff arm with a forearm which is connected with the wrist, said step of connecting a first cuff and a first cuff arm with the forearm includes connecting the first cuff arm with the forearm with an end portion of the first cuff arm adjacent to and offset to one side of the wrist, connecting a second cuff and a second cuff arm with a hand which is connected with the wrist, said step of connecting a second cuff and a second cuff arm with the hand includes connecting the second cuff arm with the hand with an end portion of the second cuff arm adjacent to and offset to the one side of the wrist and spaced from the end portion of the first cuff arm, and bending the wrist, said step of bending the wrist includes pivoting the first cuff arm about a first axis which is offset to the one side of the wrist and extends through the end portion of the first cuff arm, and pivoting the second cuff arm about a second axis which is spaced from the first axis and is offset to the one side of the wrist.

32. A method as set forth in claim 31 wherein said step of bending the wrist includes manually moving a member relative to the wrist, and transmitting force from the member to the first and second cuff arms.

33. A method as set forth in claim 32 wherein said step of manually moving a member is performed by the person having the wrist.

34. A method as set forth in claim 31 wherein said step of bending the wrist includes operating a mechanism in the orthosis in a first direction to bend the wrist in a direction away from an initial condition of the wrist, interrupting operation of the mechanism in the orthosis for a period of time, and, thereafter, resuming operation of the mechanism in the orthosis in the first direction to resume bending of the wrist in the direction away from the initial condition.

35. A method as set forth in claim 31 wherein said step of bending the wrist includes moving an actuator member along a path which extends between and is perpendicular to the first and second axes.

36. A method as set forth in claim 31 wherein said step of bending the wrist includes moving one of the first and second cuffs along one of the first and second cuff arms in a direction toward the wrist.

37. A method as set forth in claim 31 wherein said step of bending the wrist includes operating a mechanism in the orthosis, transmitting force from the mechanism to the first cuff arm to pivot the first cuff arm about the first axis, and transmitting force from the mechanism to the second cuff arm to pivot the second cuff arm about the second axis.

38. A method as set forth in claim 37 wherein said step of bending the wrist includes transmitting force from the mechanism to the first cuff to move the first cuff along the first cuff arm toward the wrist and transmitting force from the mechanism to the second cuff to move the second cuff along the second cuff arm toward the wrist.

39. A method as set forth in claim 37 wherein said step of operating a mechanism includes rotating a threaded member about an axis which extends perpendicular to said first and second axes and extends through the wrist.

40. A method of using an orthosis to bend a wrist, said method comprising the steps of connecting a first cuff and a first cuff arm with a forearm which is connected with the wrist, connecting a second cuff and a second cuff arm with a hand which is connected with the wrist, and bending the wrist, said step of bending the wrist includes moving an actuator member away from the wrist along a path which extends through the wrist, transmitting force from the actuator member to the first cuff arm to pivot the first cuff arm as the actuator member moves away from the wrist, and transmitting force from the actuator member to pivot the second cuff arm as the actuator member moves away from the wrist.

41. A method as set forth in claim 40 wherein said step of moving an actuator member away from the wrist includes rotating a threaded member about an axis which extends through the wrist.

42. A method as set forth in claim 40 wherein said step of transmitting force from the actuator member to the first cuff arm includes transmitting force through a first link which is pivotally connected with the actuator member and is pivotally connected with the first cuff arm, pivoting the first link about a pivot connection between the first link and the actuator member, and pivoting the first link about a pivot connection between the first link and the first cuff arm, said step of transmitting force from the actuator member to the second cuff arm includes transmitting force through a second link which is pivotally connected with the actuator member and the second cuff arm, pivoting the second link about a pivot connection between the second link and the actuator member, and pivoting the second link about a pivot connection between the second link and the second cuff arm.

43. A method as set forth in claim 40 wherein said step of moving an actuator member along a path which extends through the wrist includes manually moving an input member relative to the wrist.

44. A method as set forth in claim 43 wherein said step of manually moving an input member is performed by the person having the wrist.

45. A method as set forth in claim 40 wherein said step of bending the wrist includes moving one of the first and second cuffs along one of the first and second cuff arms in a direction toward the wrist ;under the influence of force transmitted from the actuator member to the one cuff.

46. A method as set forth in claim 40 wherein said step of bending the wrist includes transmitting force from the actuator member to the first cuff, moving the first cuff along the first cuff arm under the influence of the force transmitted to the first cuff from the actuator member, transmitting force from the actuator member to the second cuff, and moving the second cuff along the second cuff arm under the influence of the force transmitted to the second cuff from the actuator member.

47. A method of using an orthosis to bend a wrist, said method comprising the steps of connecting a first cuff and a first cuff arm with a forearm which is connected with the wrist, connecting a second cuff and a second cuff arm with a hand which is connected with the wrist, and bending the wrist, said step of bending the wrist includes moving the first cuff along the first cuff arm in a direction toward the wrist and moving the second cuff along the second cuff arm toward the wrist.

48. A method as set forth in claim 47 wherein said step of bending the wrist includes pivoting the first cuff arm about a first axis which is offset to one side of the wrist and extends through an end portion of the first cuff arm simultaneously with performance of said step of moving the first cuff along the first cuff arm and pivoting the second cuff arm about a second axis which is offset to the one side of the wrist and extends through an end portion of the second cuff arm simultaneously with performance of said step of moving the second cuff along the second cuff arm.

49. A method as set forth in claim 48 wherein said step of bending the wrist includes moving an actuator member away from the wrist along a path which extends through the wrist, said step of moving the first cuff along the first cuff arm includes transmitting force from the actuator member to the first cuff, said step of moving the second cuff along the second cuff arm includes transmitting force from the actuator member to the second cuff, said step of pivoting the first cuff arm about a first axis includes transmitting force from the actuator member to the first cuff arm, said step of pivoting the second cuff arm about a second axis includes transmitting force from the actuator member to the second cuff arm.

50. A method as set forth in claim 47 wherein said step of bending the wrist includes operating a mechanism in the orthosis in a first direction to bend the wrist in a direction away from an initial condition of the wrist, interrupting operation of the mechanism in the orthosis for a period of time, and, thereafter, resuming operation of the mechanism in the orthosis in the first direction to resume bending of the wrist in the direction away from the initial condition.

\* \* \* \* \*

UNITED STATES PATENT AND TRADEMARK OFFICE
CERTIFICATE OF CORRECTION

PATENT NO. : 5,503,619
DATED : April 2, 1996
INVENTOR(S) : Peter M. Bonutti

It is certified that error appears in the above-indentified patent and that said Letters Patent is hereby corrected as shown below:

Column 17, line 24, after "wrist" delete --;--.

Signed and Sealed this

Thirteenth Day of August, 1996

Attest:

BRUCE LEHMAN

Attesting Officer

Commissioner of Patents and Trademarks